United States Patent [19]

Tsujimoto et al.

[11] 4,302,396
[45] Nov. 24, 1981

[54] CHLORINATED 4-METHYLPHTHALIC ANHYDRIDES

[75] Inventors: Michihiro Tsujimoto, Tachikawa; Tsutomu Nishizawa, Kamakura; Kiyoharu Hasegawa, Yokohama; Nobuyoshi Abe, Machida, all of Japan

[73] Assignee: Mitsui Toatsu Chemicals, Incorporated, Tokyo, Japan

[21] Appl. No.: 886,563

[22] Filed: Apr. 24, 1978

[30] Foreign Application Priority Data

Apr. 6, 1977 [JP] Japan .................................. 52-38563

[51] Int. Cl.³ ..................... C07C 63/16; C07D 307/89
[52] U.S. Cl. .................................. 260/346.3; 562/480; 260/365; 260/326 C
[58] Field of Search ................ 260/515 A, 546, 346.3; 562/480

[56] References Cited

U.S. PATENT DOCUMENTS 3,098,095 7/1963 Knobloch et al. ................. 260/525
3,232,737 2/1966 Willard et al. ....................... 71/112
3,940,419 2/1976 Diehl et al. ......................... 424/274

OTHER PUBLICATIONS

Venkataraman, *The Chemistry of Synthetic Dyes*, vol. 1, pp. 140, 142, 160-163 (1952), Academic Press, Inc., New York.
Chemical Abstracts vol. 44, column 2,561(g) (1950).
Chemical Abstracts vol. 45, column 2,442(e) (1951).
Chemical Abstracts. vol. 73, column 136,771(s) (1970).
Chemical Abstracts vol. 28, column 1,339$^4$ (1934).
Chemical Abstracts vol. 26, column 135$^8$ (1932).
Chemical Abstracts vol. 68, column 104,957(n) (1968).
Chemical Abstracts vol. 47, column 543(i), 544(a).

*Primary Examiner*—Joseph E. Evans
*Attorney, Agent, or Firm*—Cushman, Darby & Cushman

[57] ABSTRACT

Novel chlorinated 4-methylphthalic acids or anhydrides of the general formula

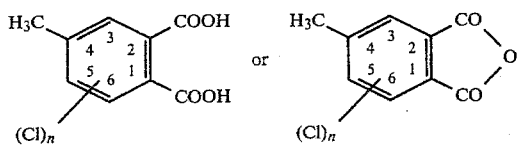

wherein n is an integer of 1, 2 or 3, with the proviso that when n is 1, the chlorine atom is positioned at 3- or 5-position and when n is 2, the chlorine atoms are positioned at 3- and 5-positions. The new compounds are produced by dissolving 4-methylphthalic anhydride in concentrated sulfuric acid or fuming sulfuric acid to form a solution, and reacting the solution with chlorine at room temperature preferably in the presence of a catalytic amount of iodine, thereby to yield a crude product containing a mixture of chlorinated 4-methylphthalic acids. By subjecting the mixture to a thermal dehydration treatment in an inactive organic solvent, each of the chlorinated compounds may be isolated as its corresponding anhydride in the form of crystals.

These chlorinated 4-methylphthalic anhydrides are valuable as intermediates for the preparation of dyestuffs or pigments.

1 Claim, No Drawings

CHLORINATED 4-METHYLPHTHALIC ANHYDRIDES

BACKGROUND OF THE INVENTION

1. Field of the Invention

This invention relates to new chlorinated 4-methylphthalic acids or anhydrides useful as intermediates for dyestuffs or pigments, and a process for preparating same.

2. Description of the Prior Art

As chlorinated derivatives of phthalic anhydride, there are known 3-chlorophthalic anhydride, 5-chlorophthalic anhydride, 3,6-dichlorophthalic anhydride, 3,4,5,6-tetrachlorophthalic anhydride and the like. 4-Methylphthalic acid or anhydride is also known. Chlorinated 4-methylphthalic acid or anhydride is, however, not hitherto known. Namely, neither of phthalic anhydride derivatives having one methyl group and one through three chlorine atoms on its benzene nucleus nor a process for the preparation of same has been known in the art.

SUMMARY OF THE INVENTION

The present invention provides new chlorinated 4-methylphthalic acids or anhydrides of the general formula:

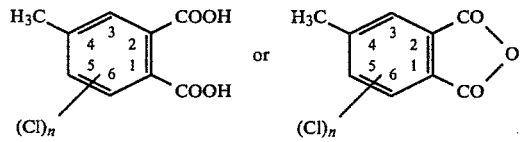

wherein n is an integer of 1 through 3, with the proviso that when n is 1, the chlorine atom is positioned at 3- or 5-position and when n is 2, the chlorine atoms are positioned at 3- and 5-positions. Specifically, these compounds are 3-chloro-4-methylphthalic acid, 5-chloro-4-methylphthalic acid, 3,5-dichloro-4-methylphthalic acid, 3,5,6-trichloro-4-methylphthalic acid, and their corresponding anhydrides.

According to the present invention, there is further provided a process for preparing the above chlorinated 4-methylphthalic acids or anhydrides. The process includes dissolving 4-methylphthalic anhydride in concentrated sulfuric acid or fuming sulfuric acid to form a solution, and reacting the solution with chlorine gas. The chlorination is favorably accelerated by a catalytic amount of iodine. The concentrated sulfuric acid preferably has a concentration of at least 90 wt %, and the fuming sulfuric acid preferably contains up to 30 wt % of sulfuric anhydride. Either the sulfuric acid is used in an amount of preferably 1 to 10 parts by weight per one part by weight of 4-methylphthalic anhydride. Iodine is used in an amount of preferably 0.01 to 10 wt % of the 4-methylphthalic anhydride. Chlorination is preferably carried out at a temperature of −20° to +60° C. Chlorine is reacted in an amount of about 1 to about 3 moles per one mole of 4-methylphthalic anhydride.

After the chlorination is terminated, the reaction mixture is poured in water to precipitate chlorinated 4-methylphthalic acids. The crude product contains a mixture of mono, di and trichloro compounds. The content of each of the chlorinated compounds varies according to the amount of chlorine gas reacted. A crude product containing mainly di or trichloro compounds is subjected to recrystallization with an inactive organic medium to give 3,5-dichloro-4-methylphthalic anhydride or 3,5,6-trichloro-4-methylphthalic anhydride. A crude product mainly containing a mixture of 3- and 5-monochloro compounds is heated to 90°–95° C. in an inactive organic solvent, thereby to separate the mixture into 3-chloro-4-methylphthalic anhydride dissolved in the solvent and 5-chloro-4-methylphthalic anhydride as a precipitate.

We have found that these chlorinated 4-methylphthalic anhydrides may serve as useful intermediates for the preparation of dyestuffs or pigments.

It is an object of this invention to provide new chlorinated derivatives of 4-methylphthalic acids or anhydrides, which are useful as intermediates for dyestuffs or pigments.

Another object of this invention is to provide a process which permits the chlorination of 4-methylphthalic anhydride in a simple and effective manner.

Other objects, features and advantages of the present invention become apparent from the detailed description of the preferred embodiments, which follows.

DETAILED DESCRIPTION OF THE PREFERRED EMBODIMENT OF THE INVENTION

4-Methylphthalic anhydride employed as a starting material for preparing the chlorinated 4-methylphthalic acids or anhydrides according to the present invention, may be prepared, for example, from methylanthranilic acid by the following known reaction route.

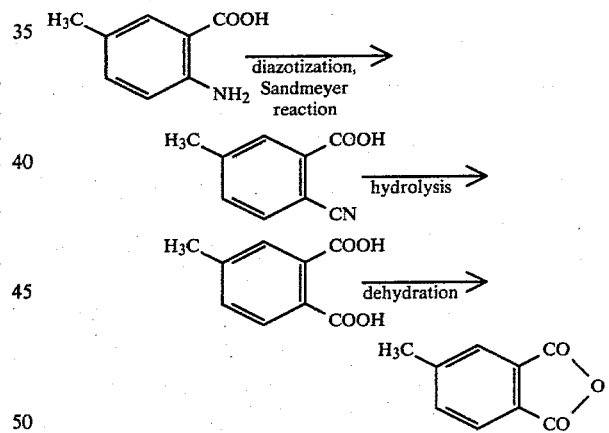

4-Methylphthalic anhydride is also able to be prepared by dehydrogenation, with sulfur, of tetrahydro-4-methylphthalic anhydride obtained from the reaction between isoprene and maleic anhydride:

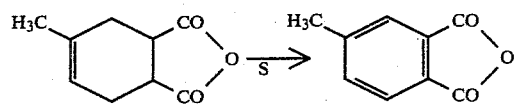

In place of 4-methylphthalic anhydride, 4-methylphthalic acid may also be used as a starting material in the process of this invention. In this case, since 4-methylphthalic acid undergoes dehydration during the chlorination stage to produce water which tends to lower the concentration of concentrated sulfuric acid or fuming sulfuric acid, it is necessary to use sulfuric acid with higher concentration for the compensation purpose.

As a reaction medium for the chlorination of 4-methylphthalic anhydride or acid, concentrated sulfuric acid or fuming sulfuric acid is employed. For the chlorination of 4-methylphthalic anhydride the concentration of concentrated sulfuric acid is preferably at least 90 wt %. With sulfuric acid of lower than 90%, the chlorination does not practically proceed. In the case of fuming sulfuric acid, the higher the content of sulfuric anhydride, the faster is the chlorination rate. However, an excess sulfuric anhydride concentration is not advantageous because such fuming sulfuric acid is not easy to be handled and the reaction mixture is not kept homogeneous due to formation of precipitates. Accordingly, for the convenience of reaction operation, it is preferred that the content of sulfuric anhydride in fuming sulfuric acid be not higher than 30 wt %, more preferably in the range of 10-20 wt %.

The amount of concentrated or fuming sulfuric acid used for dissolving the starting material has not great influence upon the chlorination. It is advantageous, however, to use such sulfuric acid in an amount of 1 to 10 parts by weight per one part by weight of 4-methylphthalic anhydride, and specifically, in the case of fuming sulfuric acid containing 10-20 wt % of sulfuric anhydride, the amount is preferably 1-5 parts by weight, in that the starting material can be readily dissolved and that recovery step of final products can be easily conducted.

In order for the chlorination to proceed effectively, it is preferred that iodine be used as catalyst. The amount of iodine used is generally 0.01-10% by weight of 4-methylphthalic anhydride, preferably 1-5% by weight. The speed of the chlorination is slow in the absence of iodine.

When the chlorination is carried out at an elevated temperature, undesirable side reactions occur. On the other hand, when performed at an extremely low temperature, the dissolution of the starting material and agitation of the reaction mixture cannot be effectively made. Accordingly, the reaction is generally conducted at a temperature of $-20°$ to $+60°$ C. Because reaction temperature within the above range has not great influence upon reaction rate, it is preferred that the chlorination be performed at a visinity of room temperature, namely from 10° to 30° C.

In a preferred aspect, 4-methylphthalic anhydride and iodine are first dissolved in the above-described sulfuric acid, with which chlorine is brought into contact with stirring at the above-described temperature to permit the chlorination to proceed. The contacting step may include either blowing chlorine gas into the anhydride-containing solution placed in a reaction vessel having an open end, or feeding chlorine gas under a pressure of 0-10 Kg/cm$^2$(Gauge) to a reaction vessel having a closed end and being provided with the reaction solution.

The amount of chlorine reacted with 4-methylphthalic anhydride may vary from about 1 to 3 moles per mole of the anhydride. The constitution of chlorinated products depends upon the amount of the reacted chlorine. That is, when chlorine is reacted in a relatively small amount, such as about 1 mole per mole of 4-methylphthalic anhydride, then major chlorinated product will be monosubstituted compounds accompanying a small amount of disubstituted compounds and unreacted anhydride. As the amount of reacted chlorine increases, the selectivity to monosubstituted product proportionally decreases but di and trisubstituted compounds increase. The main dichlorinated product is 3,5-dichloro compound. With further increase of reacted chlorine, the yield of disubstituted compounds increases to reach to a maximum, and then begins to decrease. The content of trisubstituted compound in the chlorinated products increases as the amount of the reacted chlorine increases. Thus, when the reacted chlorine amounts to about 3 moles per mole of 4-methylphthalic anhydride, the chlorinated product is predominantly trisubstituted compound.

The above-described change in the constitution of the chlorinated products by the amount of reacted chlorine is able to be easily known by analyzing the composition of reaction solutions by means of gas-chromatography. In table 1 shown below, retention time of each of the chlorinated 4-methylphthalic anhydrides and related compounds is shown, which was obtained under the following gas-chromatographic conditions.

apparatus: Shimadzu Gas Chromatograph GC-6A (made by Shimadzu Seisakusho, Japan)

column: 3 mm $\phi \times 3$ m column packing: Celite 525 (a chemical product of kieselguhr, made by Johns Manville Products Corp., U.S.A.)-10% OV-101 (a silicone resin, made by OHIO VALLEY SPECIALITY CHEMICAL INC.)

column temperature: 170° C.

carrier gas: helium, 40 ml/min

In practising the process of the present invention, the amount of chlorine to be reacted is controlled according to the end product aimed at. For example, in case where monosubstituted compounds are intended to be prepared, feeding of chlorine gas is stopped when approximately 1 mole, i.e. 0.8-1.1 moles of chlorine have been reacted with 4-methylphthalic anhydride, whereby to obtain a crude chlorinated product containing monochlorinated compounds as a main product and a small amount of unreacted 4-methylphthalic anhydride and dichlorinated compounds. The monochlorinated product consists of 3-chloro and 5-chloro compounds. Crude chlorinated product containing mainly trichlorinated compound is able to be obtained by allowing chlorine to react with 4-methylphthalic anhydride in an amount of about 3 moles, i.e. 2.5-3 moles per mole of the anhydride. To obtain crude chlorinated product containing mainly dichlorinated compounds, chlorine is permitted to react until the concentration of dichlorinated compounds in the reaction mixture has reached to a maximum, which is able to be known by gas chromatographic analysis on the reaction solution. The main dichlorinated product is 3,5-dichlorinated compound. A small amount of 3,6- and 5,6-dichlorinated isomers are also produced.

After the chlorination is terminated by stopping the feeding of chlorine gas, the reaction mixture is poured in water to recover crude chlorinated product of 4-methylphthalic acids as a solid.

As described above, this crude chlorinated product is a mixture of a main component and minor other components. The product may be used as is, in some cases. If necessary, however, a single chlorinated compound may be isolated from the crude chlorinated product in various manners.

For example, a crude chlorinated product mainly containing di or trichloro acid is heated in an inactive organic medium to convert the acid into corresponding anhydride by dehydration, which is then recrystallized with the same or another inactive organic medium, thereby to isolate 3,5-dichloro-4-methylphthalic anhydride or 3,5,6-trichloro-4-methylphthalic anhydride as crystals. To separate 3-chloro and 5-chloro compounds from a crude chlorinated product mainly composed of monochlorinated compounds, the crude product is first heat-treated at 90°-95° C. in an inactive organic medium. As a consequence, the 3-chloro compound undergoes dehydration to form corresponding anhydride which is dissolved in the medium, whereas the 5-chloro isomer is remained undissolved since it hardly undergoes dehydration at such temperature. The heat-treated mixture is then separated into solid and a filtrate by filtration. 3-Chloro-4-methylphthalic anhydride is obtained from the filtrate by distilling off the organic medium. By treating the solid in an inactive organic medium at 100° C. or more, 5-chloro-4-methylphthalic acid is converted into corresponding anhydride to give a solution, from which the anhydride is recovered as crystals by cooling.

Examples of the inactive organic medium useful for conducting the above-described isolation are an aromatic hydrocarbon such as benzene, toluene and xylene; a halogenated aliphatic hydrocarbon such as carbon tetrachloride, ethylene dichloride, trichloroethane and tetrachloroethane; an aliphatic petroleum naphtha such as ligroin, petroleum ether, benzine.

These chlorinated 4-methylphthalic anhydrides are thus obtained in the form of crystals and have inherent melting points as shown in table 1. Proton NMR absorption spectra of these anhydrides show a clear peak assigned to the absorption of the methyl group on their benzene ring. The chemical shifts of the absorption peak of the anhydrides are also shown in terms of $\tau$ values in table 1.

These anhydrides are soluble in a nonpolar organic solvent such as benzene and xylene at an elevated temperature. They are also soluble in boiling water. When such aqueous hot solutions are cooled under an acidic condition, using sulfuric acid or hydrochloric acid, corresponding chlorinated 4-methylphthalic acids may be obtained as crystals. By this, 3-chloro-4-methylphthalic acid (m.p.: 181.5°-182.5° C., decomp.), 5-chloro-4-methylphthalic acid (m.p.: 209.5°-210.5° C., decomp.) 3,5,6-trichloro-4-methylphthalic acid (m.p.: 222°-224° C., decomp.), etc. may be obtained. These acids are soluble in water and sparingly soluble in nonpolar organic solvents.

TABLE 1

| Compound | Retention times* (min.) | m.p. (°C.) | $\tau$ Values** (ppm) |
|---|---|---|---|
| H3C—[ring]—CO\O/CO (related compd.) | 5.5 | — | — |
| ClH2C—[ring]—CO\O/CO (related compd.) | 13.5 | — | — |
| H3C—[ring](Cl)—CO\O/CO | 9.5 | 152-154 | 7.42 |

TABLE 1-continued

| Compound | Retention times* (min.) | m.p. (°C.) | $\tau$ Values** (ppm) |
|---|---|---|---|
| H3C—[ring](Cl)—CO\O/CO | 11.5 | 133-135 | 7.42 |
| H3C—[ring](Cl,Cl)—CO\O/CO | 23 | 125-127 | 7.3 |
| H3C—[ring](Cl,Cl,Cl)—CO\O/CO | 41 | 219-221 | 7.3 |

*Retention time of chlorinated 4-methylphthalic acids are the same as corresponding anyhydrides.
**Chemical shift of methyl group in NMR absorption spectra of anhydrides in CDCl3 (60 MC apparatus).

The chlorinated 4-methylphthalic acids and anhydrides of the present invention are useful intermediates for dyestuffs or pigments. For example, 3-chloro-4-methylphthalic anhydride gives 1-chloro-2-methylanthraquinone which is known as an important intermediate for a known vat dye, pyranthrone.

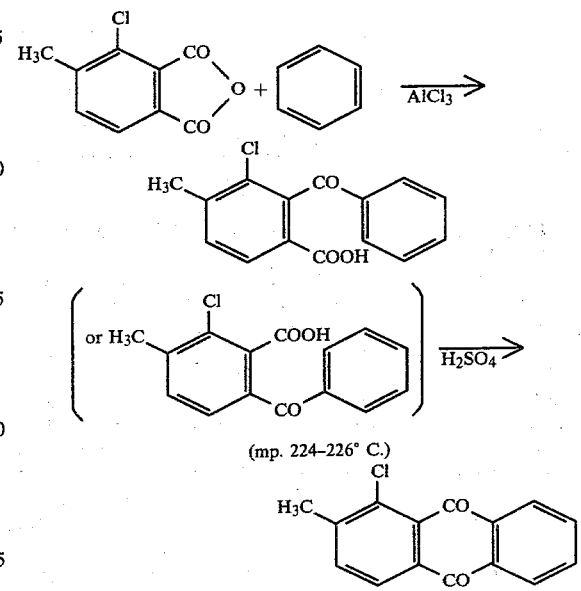

(mp. 224-226° C.)

From 3,5,6-trichloro-4-methylphthalic anhydride, 1,3,4-trichloroanthraquinone-2-carboxylic acid is obtained as shown below.

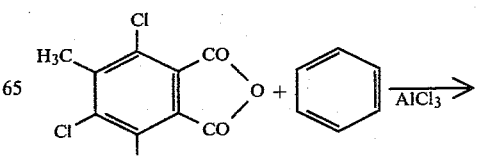

-continued

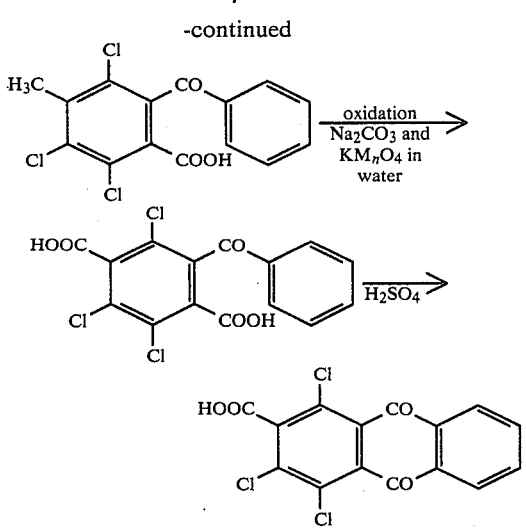

This anthraquinonecarboxylic acid gives, via 1,4-diamino-3-chloroanthraquinone-2-carboxylic acid, a blue dye of the following general formula which is useful as a disperse dye for polyesters.

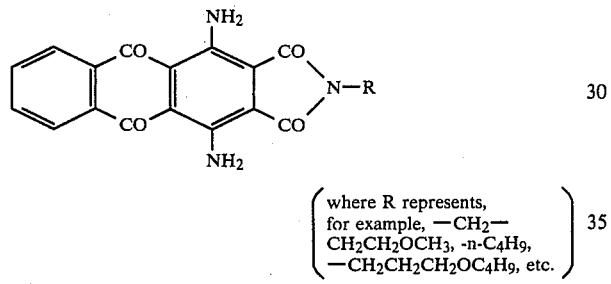

(where R represents, for example, —CH$_2$—CH$_2$CH$_2$OCH$_3$, -n-C$_4$H$_9$, —CH$_2$CH$_2$CH$_2$OC$_4$H$_9$, etc.)

The following example will further illustrate the process of this invention, in which parts are by weight.

EXAMPLE 1

Preparation of 3-chloro-4-methylphthalic anhydride and 5-chloro-4-methylphthalic anhydride:

10 Grams of 4-methylphthalic anhydride, 0.1 g of iodine and 50 g of fuming sulfuric acid having the sulfuric anhydride content of 5 wt % were mixed, in which chlorine gas was blown at a feed rate of 7 ml/min with stirring. Feeding of chlorine gas was stopped when 0.062 mole of chlorine had been reacted with the anhydride. Then, the reaction mixture was poured into 250 g of water, cooled to effect precipitation. The precipitate was washed with a small amount of water and dried at 70° C. to give 9.2 g of a crude chlorinated product. Gas chromatographic analysis, conducted under the above-described conditions, revealed that the product consisted of 33.1 wt % of 5-chloro-4-methylphthalic acid, 42.8 wt % of 3-chloro isomer, 6.1 wt % of 3,5-dichloro compound, and 1.6 wt % of other compounds. Monosubstituted compounds were isolated from the crude mixture in the following manner. A mixture of 1 part of the crude product and 10 parts of xylene was heated at 90°–95° C. for 7 hours with stirring. The resulting hot mixture was then filtered to separate the mixture into a filtrate and solid mainly consisting of 5-chloro-4-methylphthalic acid. Xylene was distilled off from the filtrate and the distillation bottom was subjected to recrystallization with xylene several times, thereby obtaining substantially pure 3-chloro-4-methylphthalic anhydride in the form of colorless prismatic or pillared crystals. The 3-chloro product was found to have a melting point of 133°–135° C. The solid was added to xylene, which was refluxed to give a solution. The solution was cooled to effect precipitation. The resulting precipitate was subjected to repeated crystallization with xylene, thereby obtaining substantially pure (purity 99.9% or more by gas chromatographic analysis) 5-chloro-4-methylphthalic anhydride in the form of colorless hexahedral or thick platy crystals having a melting point of 152°–154° C. The chemical shifts, in terms of $\tau$ values, of the methyl group in proton NMR absorption spectrum of each of the monochloro products were found to be 7.42 ppm (in CDCl$_3$).

EXAMPLE 2

Preparation of 3,5-dichloro-4-methylphthalic anhydride:

The chlorination reaction described in Example 1 was repeated and continued until the component showing the retention time of 23 min., by means of gas chromatography under the above-described conditions, had amounted to about 30% by weight of the reaction mixture; the maximum yield of di-substituted compounds was achieved. A crude chlorinated product was obtained by the procedure described in Example 1. 5 Parts of a mixed benzene-toluene solvent (1:1) were mixed with 1 part of the crude product, which was refluxed for 30 min. The resulting mixture was filtered to separate it into a filtrate and solid. A greater part of monosubstituted compounds was found to be present in the solid, while di and trisubstituted compounds to be contained in the filtrate. The filtrate was dried up and recrystallization was effected with xylene whereby the trisubstituted compound was separated as crystals. The mother liquor was repeatedly subjected to the alternate drying up and recrystallization treatments to purify the disubstituted compound. Final recrystallization was performed with ligroin to obtain 3,5-dichloro-4-methylphthalic anhydride in the form of platy crystals having a melting point of 125°–127° C. NMR absorption spectrum showed the absorption of the methyl group at $\tau$ values of 7.3 ppm.

EXAMPLE 3

Preparation of 3,5,6-trichloro-4-methylphthalic anhydride:

20 Grams of 4-methylphthalic anhydride, 100 g of concentrated sulfuric acid having concentration of 100 wt % and 0.2 g of iodine were mixed, to which was fed chlorine gas at a rate of 20 ml/min. for 37 hours. At the end of the chlorination, the trichloro compound was partly precipitated. The reaction mixture was poured in 500 g of water followed by the same treatment as in Example 1, thereby quantitatively giving a crude chlorinated product. The crude product was found through a gas chromatographic analysis to contain 9.4 wt % of 5-chloro-4-methyl compound, 2.4 wt % of 3-chloro-4-methyl compound, 16.9 wt % of dichloro compounds and 69.5 wt % of trichloro compound. The crude chlorinated product was 5 times recrystallized with xylene to give 3,5,6-trichloro-4-methylphthalic anhydride in the form of hexahedral or thick platy crystals having a melting point of 219°–221° C. NMR spectrum of the trisubstituted anhydride showed the absorption of its methyl group at $\tau$ values of 7.3 ppm.

What is claimed is:
1. 3,5,6-Trichloro-4-methylphthalic acid or its anhydride.

* * * * *